United States Patent
Ramirez-Vick

(12) 
(10) Patent No.: US 7,270,954 B1
(45) Date of Patent: *Sep. 18, 2007

(54) HYBRIDIZATION OF TARGET DNA WITH IMMOBILIZED NUCLEIC ACID ANALOGS

(75) Inventor: Jaime E. Ramirez-Vick, Mayagüez, PR (US)

(73) Assignee: Iris Biotechnologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/333,697

(22) PCT Filed: Jun. 30, 2000

(86) PCT No.: PCT/US00/18181

§ 371 (c)(1),
(2), (4) Date: Feb. 24, 2003

(87) PCT Pub. No.: WO01/01144

PCT Pub. Date: Jan. 4, 2001

(51) Int. Cl.
*C12Q 1/68* (2006.01)

(52) U.S. Cl. .......................................................... 435/6

(58) Field of Classification Search ................... 435/6, 435/7, 94, 518, 4, 7.1, 7.4–7.95, 283.1–289.1, 435/973; 536/24.3, 25.3; 436/514, 523–528; 422/50–73
See application file for complete search history.

(56) References Cited

U.S. PATENT DOCUMENTS

| | | | | |
|---|---|---|---|---|
| 4,895,955 A | * | 1/1990 | Ford et al. ............... | 548/304.1 |
| 4,896,955 A | * | 1/1990 | Zider et al. .................... | 351/41 |
| 5,077,210 A | | 12/1991 | Eigler et al. | |
| 5,279,558 A | * | 1/1994 | Kriesel ........................ | 604/85 |
| 5,412,087 A | | 5/1995 | McGall et al. | |
| 5,465,151 A | | 11/1995 | Wybourne et al. | |
| 5,491,097 A | | 2/1996 | Ribi et al. | |
| 5,532,128 A | | 7/1996 | Eggers et al. | |
| 5,620,850 A | | 4/1997 | Bamdad et al. | |
| 5,622,826 A | * | 4/1997 | Varma ............................ | 435/6 |
| 5,760,130 A | | 6/1998 | Johnston et al. | |
| 5,837,860 A | | 11/1998 | Anderson et al. | |
| 5,942,397 A | * | 8/1999 | Tarlov et al. ................... | 435/6 |
| 6,174,683 B1 | * | 1/2001 | Hahn et al. ...................... | 435/6 |
| 6,197,515 B1 | * | 3/2001 | Bamdad et al. ................. | 435/6 |
| 6,355,421 B1 | * | 3/2002 | Coull et al. ..................... | 435/6 |
| 6,500,609 B1 | * | 12/2002 | Ribeill et al. ................... | 435/4 |
| 6,537,749 B2 | * | 3/2003 | Kuimelis et al. ............... | 435/6 |
| 6,613,508 B1 | * | 9/2003 | Ness et al. ....................... | 435/6 |
| 6,777,544 B2 | * | 8/2004 | Uhlmann et al. ........... | 536/22.1 |
| 7,005,419 B1 | * | 2/2006 | Wang et al. ................... | 514/12 |
| 7,108,971 B2 | * | 9/2006 | Ramirez-Vick ................ | 435/6 |
| 2002/0009723 A1 | * | 1/2002 | Hefti .............................. | 435/6 |
| 2002/0160391 A1 | * | 10/2002 | Ramirez-Vick ................ | 435/6 |

OTHER PUBLICATIONS

Perry-O'Keefe et al, Peptide nucleic acid pre-gel hybridization: an alternative to Southern hybridization, 1996, Genetics, 93, 14670-75.*

Folch et al, High-vacuum versus "environmental" electron beam deposition, 1996, J Vac Sci Tech B 14(4), 2609-2614.*

*Molecular Biology of the Cell, Fourth Edition,* Alberts et al., 2002, published by Garland Science, New York, NY, Fig. 8-62.

Thiel, et al., "In Situ Surface Plasmon Resonance Imaging Detection of DNA Hybridization to Oligonucleotide Arrays on Gold Surfaces", Anal. Chem., vol. 69, pp. 4948-4956, 1997.

Wang et al., "Peptide Nucleic Acid Probes for Sequence-Specific DNA Biosensors", J. Am. Chem. Soc., vol. 118, pp. 7667-7670, 1996.

Dorland's Illustrated Medical Dictionary, 28th ed., W. B. Saunders Company (1994).

* cited by examiner

*Primary Examiner*—Ann Yen Lam
(74) *Attorney, Agent, or Firm*—James A. Fox, Esq.; Heller Ehrman LLP

(57) ABSTRACT

This invention is related to the immobilization of peptide nucleic acids (PNAs) onto solid surfaces for use in hybridization, purification, biosensing, and other biochemical applications. Specifically, their use to increase the thermal stability, specificity, and lifetime of devices based on in situ hybridization is disclosed. A method is disclosed by which peptide nucleic acids replace oligonucleotides as probes in the detection of specific DNA and RNA sequences.

14 Claims, No Drawings

HYBRIDIZATION OF TARGET DNA WITH IMMOBILIZED NUCLEIC ACID ANALOGS

FIELD OF THE INVENTION

This invention relates to the use of peptide nucleic acids and analogs in hybridization reactions, particularly on microarrays.

BACKGROUND

Deoxyribonucleic acid (DNA) and ribonucleic acid (RNA) are macromolecules built up from simple monomeric subunits called nucleotides. The nucleotide has the following three components: 1) a cyclic five-carbon (pentose) sugar (deoxyribose for DNA, and ribose for RNA), 2) a nitrogenous base of either purine or pyrimidine derivation, covalently attached to the I'-carbon atom of the sugar by a N-glycosylic bond, and 3) a phosphate attached to the 5' carbon of the sugar by a phosphodiester bond. The purines are adenine (A) and guanine (G), while the pyrimidines are cytosine (C) and thymine (T) for DNA, and cytosine (c) and uracil (U) for RNA.

The nucleotides of DNA are called deoxyribonucleotides, whereas those of RNA are called ribonucleotides. Each nucleotide contains both a specific and a nonspecific region. The phosphate and sugar groups are the nonspecific portions of the nucleotide, while the purine and pyrimidine bases make up the specific portion. Nucleotides are joined to one another linearly by a chemical bond between atoms in the nonspecific regions to form polynucleotides. The linkage, called a phosphodiester bond, is between a phosphate group and a hydroxyl group on the sugar component.

The most important feature of DNA is that it usually consists of two complementary strands coiled about one another to form a double helix. There are ten nucleotides on each chain for every turn of the helix. The two chains are joined together through a combination of van der Waals forces and hydrogen bonds between the purine and pyrimidine base pairs on complementary strands. This base pairing is so specific that adenine binds only to thymine and guanine only to cytosine. This base pairing provides stabilization by hydrogen bonding between complementary bases.

Furthermore, this specificity of base pairing is what permits the transmission of genetic information from one generation to another. When cell replication occurs, the DNA double helix unwinds, and two new complementary DNA strands are formed. The sequence of bases (A, G, T, and C) in a strand of DNA specifies which amino acids are assembled in what order to form proteins. Each amino acid is encoded by a three base sequence of nucleotides, known as a codon; the correlation between each amino acid and its codon is known as the genetic code. The code is degenerate in that several different codons encode the same amino acid.

This base-pairing interaction can be mimicked in vitro by first denaturing the DNA and then allowing it to re-form. DNA is denatured in an aqueous solution by heating to about 100° C. (or pH>13). This disrupts the bonds between the two complementary strands dissociating the double helix into two single strands. These single strands will re-form into a DNA double helix if kept for a prolonged period of time at 65° C. by a process called DNA renaturation or hybridization. Similar hybridization reactions will occur between any two single stranded nucleic acid chains (DNA:DNA, RNA:RNA, or DNA:RNA), provided that they have a complementary nucleotide sequence.

The enormous specificity of this hybridization reaction allows any single-stranded sequence of nucleotides to be labeled with a radioisotope or fluorophore and used as a probe to find a complementary partner strand. Probes of this type are widely used to detect the nucleic acids corresponding to specific genes in situ, by a procedure called in situ hybridization. In situ hybridization is only an example of many other biochemical applications which use base pair specificity.

A complementary artificial DNA/RNA analog has been synthesized and named peptide nucleic acid (PNA)(Nielsen, et al., *Science* 254:1496-1500, 1991). A representative PNA is a 2-aminoethyl glycine linked by a methylenecarbonyl linkage to one of the four bases (A, G, T, or C) found in DNA. Like amino acids, these molecules have amino and carboxyl termini. Unlike nucleotides, these molecules lack pentose sugar phosphate groups. These properties allow peptide nucleic acids to hybridize to complementary RNA or DNA with higher affinity and specificity than corresponding nucleotides.

In the art, there are several known nucleic acid analogs having nucleobases bound to backbones other than the naturally-occurring ribonucleic acids or deoxyribonucleic acids. These nucleic acid analogs have the ability to bind to nucleic acids with complementary nucleobase sequences. Among these, the peptide nucleic acids (PNAs), as described, for example, in WO 92/20702, have been shown to be useful as therapeutic and diagnostic reagents. This may be due to their generally higher affinity for complementary nucleobase sequence than the corresponding wild-type nucleic acids.

PNAs are compounds that are analogous to oligonucleotides, but differ in composition. In PNAs, the deoxyribose backbone of oligonucleotide is replaced by a peptide backbone. Each subunit of the peptide backbone is attached to a naturally-occurring or non-naturally-occurring nucleobase. One such peptide backbone is constructed of repeating units of N-(2-aminoethyl)glycine linked through amide bonds.

PNAs bind to both DNA and RNA and form PNA/DNA or PNA/RNA duplexes. The resulting PNA/DNA or PNA/RNA duplexes are bound tighter than corresponding DNA/DNA or DNA/RNA duplexes as evidenced by their higher melting temperatures ($T_m$). This high thermal stability of PNA/DNA(RNA) duplexes has been attributed to the neutrality of the PNA backbone, which results elimination of charge repulsion that is present in DNA/DNA or RNA/RNA duplexes. Another advantage of PNA/DNA(RNA) duplexes is that $T_m$ is practically independent of salt concentration. DNA/DNA duplexes, on the other hand, are highly dependent on the ionic strength.

Homopyrimidine PNAs have been shown to bind complementary DNA or RNA forming $(PNA)_2$/DNA(RNA) triplexes of high thermal stability (Egholm et al., Science, 1991, 254, 1497; Egholm et al., J. Am. Chem. Soc., 1992, 114, 1895; Egholm et al., J. Am. Chem. Soc., 1992, 114, 9677).

In addition to increased affinity, PNAs have increased specificity for DNA binding. Thus, a PNA/DNA duplex mismatch show 8° to 20° C. drop in the $T_m$ relative to the DNA/DNA duplex. This decrease in $T_m$ is not observed with the corresponding DNA/DNA duplex mismatch (Egholm et al., Nature 1993, 365, 566).

A further advantage of PNAs, compared to oligonucleotides, is that the polyamide backbone of PNAs is resistant to degradation by enzymes.

The major advantages of PNAs over DNA (or RNA) for use as in situ hybridization probes are their: (1) higher thermal stability, (2) higher specificity, and (3) resistance to degrading enzymes. The neutral backbone of the PNAs gives to PNA:DNA duplexes (or PNA:RNA) a higher thermal stability compared to DNA:DNA (or RNA:RNA) duplexes. This stronger binding is attributed to the lack of charge repulsion between the PNA strand and the DNA (or RNA) strand. Also, PNAs show a greater specificity in binding to complementary DNA (or RNA). As a result a PNA/DNA mismatch is more destabilizing than a mismatch in a DNA/DNA duplex. PNA oligomers are also resistant to degradation by proteases and nucleases since their polyamide backbone with nucleobase side chains is not a combination easily recognized by these enzymes. This extends the lifetime of any system or device in which PNAs are used.

The object of the present invention is to provide a method for the immobilization of labeled PNAs onto solid surfaces for use in hybridization, purification, biosensing, and other biochemical applications.

SUMMARY OF INVENTION

This invention is related to the immobilization of peptide nucleic acids (PNAs) onto solid surfaces for use in hybridization, purification, biosensing, and other biochemical applications. Specifically, their use to increase the thermal stability, specificity, and lifetime of devices based on in situ hybridization is disclosed. A method is disclosed by which peptide nucleic acids replace oligonucleotides as probes in the detection of specific DNA and RNA sequences.

The general process involves the use of solid substrates containing specific functionalities to which the PNAs are immobilized. The solid supports are activated by sorbing the following construct in the order given: (1) an anchor group; (2) a spacer arm; and (3) a reactive terminal group. This tripartite structure provides a stable anchor bond to the solid support, a spacer arm which gives flexibility to the PNA allowing it to interact with its environment in a way which minimizes any steric hindrance, and a reactive terminal group to immobilize the PNA.

This invention provides a ligand-binding solid support having a soft metal solid surface and a heterobifunctional spacer chemi- or physisorbed to the soft metal solid surface via soft metal-soft base bonding. Preferably the soft metal solid surface is silver, copper, gold, platinum (II), mercury, mercury (II), thallium, cadmium (II), platinum (IV) or palladium (II). The heterobifunctional spacer is preferably a hydrocarbon of chain length from about 10 to about 40 carbon atoms, having at least one soft base anchor group and at least one nucleotide binding group. The soft base anchor group is an $RSH$, $RS^-$, $R_2S$, $RSSR$, $CN^-$, $S_2O_3^{2-}$, $I^-$, $R_3P$, $(RO)_3P$, $C2H4$ or $C6H6$ group, where R is an organic group. Optionally, an oligonucleotide is pre-attached to the spacer.

This invention also provides methods for preparing a ligand-binding solid surface, by selecting a soft metal solid surface and immobilizing a heterobifunctional spacer on said solid surface via soft metal-soft base bonding.

Assay systems having soft metal solid surfaces and a heterobifunctional spacer chemi- or physisorbed to said soft metal solid surface via soft metal-soft base bonding are also provided, as are methods for detecting the presence of a biological molecule by exposing a sample containing biological molecules to a surface as defined above.

DETAILED DESCRIPTION OF THE INVENTION

Definitions

Unless indicated otherwise, the terms defined below have the following meanings:

"Anchor group" refers to the functional chemical group containing the soft base that sorbs the spacer to the soft metal surface.

"Binding density" refers to the number of reactive terminal groups per unit surface area available for binding the labeled biopolymer.

"Biopolymer" refers to biological molecules such as proteins, oligonucleotides, DNA, RNA, PNA, etc., which are the basis of hybridization, purification, immunoassays, and many other biochemical applications.

"Hybridization" refers to binding reaction between complementary partners of biopolymer molecules.

"Ligand" refers to one member of the ligand/receptor binding pair, such as, oligonucleotides, DNA, and proteins.

"Nonspecific interaction" refers to the individual physicochemical interactions (i.e., hydrogen bonds, ionic bonds, hydrophobic interactions, and van der Waals forces) where structure is not involved.

"Protein" refers to enzymes, antibodies, and any other polypeptides.

"Soft bases" refer to the species defined as having a small charge and large size and preferring to bind with soft metals.

"Soft metals" refer to the species defined as having a small charge and large size and preferring to bind with soft bases.

"Spacer arm" refers to the molecule that helps make the immobilized ligand flexible enough to make it accessible to the receptor. This is usually a long chain hydrocarbon, optionally containing heteroatoms, and having at least two functional groups.

"Specific interactions" refers to the sum total of a particular set of physico-chemical interactions where structure can play a major role. These interactions include hydrogen bonds, ionic bonds, hydrophobic interactions, and van der Waals forces.

"Steric hindrance" refers to the effect by large groups near the ligand, which limits its accessibility to the receptor molecule.

Immobilization of Molecules on Soft Metal Surfaces

This invention is related to the immobilization of labeled ligands onto solid surfaces using soft metal-soft base binding. This invention provides processes for the development of reliable techniques for immobilizing biologically active biopolymer probe molecules, obtaining high sensitivity and high selectivity, and at lower cost through reuse of sensing elements.

The general process involves the use of substrates containing soft metal thin films Heterobifunctional spacer molecules are then added. This heterobifunctional spacer is a hydrocarbon having a chain length of about 10 to about 40 carbon atoms, preferably about 15 to about 25 carbon atoms, having at least two functional groups. Of the two functional groups, one is a soft base that will sorb with the soft metal surface. The other functional group on the spacer is selected to bind the functional group on the label of the ligand. Optionally, an oligonucleotide is pre-attached to the spacer prior to sorption on the metal surface. This process creates an active solid surface that is able to bind labeled ligands in high density and with minimum nonspecific binding.

The (anchor group-spacer arm-reactive terminal moiety) structure provides a stable anchor bond to the solid surface, a spacer arm which gives flexibility to the ligand allowing it to interact with its environment in a way which minimizes any steric hindrance, and a reactive terminal moiety which binds the ligand. Optionally, an oligonucleotide may serve as the reactive terminal moiety. The choice of the individual components of this immobilization structure depends on the combination that provides a minimum in nonspecific interactions and steric hindrance, and a maximum in binding density. The type of anchor group used will provide the solid support with the proper functionality to immobilize a spacer arm with a reactive terminal group. This immobilization structure can either be built piecemeal upon the solid substrate or pre-assembled and sorbed as one unit to the surface. The soft base anchor group is an RSH, RS$^-$, R$_2$S, RSSR, CN$^-$, S$_2$O$_3^{2-}$, I$^-$, R$_3$P, (RO)$_3$P, C2H4 or C6H6 group, where R is an organic group.

The present invention also provides methods for recovering the immobilized ligands by using sulfur-containing competing molecules to displace the heterobifunctional spacers. Due to the high aqueous solubility of thiodiglycol and its thioether functional group, a high elution recovery can be accomplished using a concentrated solution of thiodiglycol. The substrate may then be reused by washing with water and ethanol followed by heating under a partial vacuum in order to drive off the relatively volatile thiodiglycol.

The sorbed molecules are bound to the solid surface by valence forces similar in strength to those involved in covalent bonds. However, unlike covalent interactions, there is a dynamic equilibrium in which adsorbed molecules can be desorbed without breaking any bonds. The interaction between soft metal ions and soft bases is described qualitatively by the principle of Hard and Soft Acids and Bases (HSAB) based on the Lewis definition of acids and bases (Pearson, R. G., Chem. Brit. 1967, 3, 103-107. Pearson, R. G., J. Chem. Ed. 1968, 45, 581-587. Pearson, R. G., J. Chem. Ed 1968, 45, 643-648). This principle states simply that hard acids prefer to coordinate with hard bases and soft acids with soft bases. It defines hard acids as those that are small in size, of high positive charge, and do not contain unshared pairs of electrons in their valence shell. These properties lead to high electronegativity and low polarizability. Soft acids are large in size, of low positive charge, and containing unshared pairs of electrons (p or d) in their valence shell. This leads to high polarizability and low electronegativity. Thus soft acids form stable complexes with bases that are highly polarizable. While hard acids, of which the proton is typical, will usually form stable complexes with bases such that polarizability plays only a minor role. Acids and bases can thus be classified according to these premises into hard, soft, or borderline (TABLE 1). Since these acid/base interactions comprise a number of different properties, there is also more than one theory which describe them. These theories are the ionic-covalent, the π-bonding, and the electron correlation theories.

TABLE 1

CLASSIFICATION OF LEWIS ACIDS AND BASES

| Class | Acids | Bases[¶] |
|---|---|---|
| Hard | H, Li, Na, K, Be$^2$, Mg$^2$, Ca$^2$, Sr$^2$, Fe$^3$ | H$_2$O, OH$^-$, F$^-$, Cl$^-$, CH$_3$COO$^-$, SO$_4^{2-}$, NO$_3^-$, ROH, RO$^-$, NH$_3$, RNH$_2$ |

TABLE 1-continued

CLASSIFICATION OF LEWIS ACIDS AND BASES

| Class | Acids | Bases[¶] |
|---|---|---|
| Borderline | Cu$^2$, Zn$^2$, Ni$^2$, Fe$^2$, Co$^2$, Pb$^2$, Sn$^2$, Sb$^3$ | C$_6$H$_5$NH$_2$, C$_5$H$_5$N, N$_3^-$, Br$^-$, NO$_2^-$, SO$_3^{2-}$ |
| Soft | Ag, Cu, Au, Pt$^2$, Hg, Hg$^2$, Tl, Cd$^2$, Pt$^4$, Pd$^2$ | RSH, RS$^-$, R$_2$S, CN$^-$, S$_2$O$_3^{2-}$, I$^-$, R$_3$P, (RO)$_3$P, C$_2$H$_4$, C$_6$H$_6$ |

[¶]R stands for alkyl group, e.g., CH$_3$, C$_2$H$_5$, etc.

The ionic-covalent theory is the oldest and the most obvious. It states that hard acids interact with hard bases mainly by ionic forces because of their small size and high charge. Soft acids and bases with their large size and small charge cannot form a stable complex through ionic forces. The π-bonding theory states that soft acids (usually metals) with loosely held d-orbital electrons can form π bonds with soft bases that contain empty d-orbitals. Finally, the electron correlation theory suggests that London or Van der Waals dispersion energies between atoms or groups in the same molecule may lead to the stabilization of the molecule. These forces are large in complexes formed by highly polarizable soft acids and bases, thus providing additional stability.

The various methodologies mentioned in this disclosure are well-known to those skilled in the art. Such methodologies can be found in standard references such as: Hermanson, G. T., Bioconjugate Techniques, 1996, Academic Press, San Diego, Calif.; Birren, B., et al., Genome Analysis: A Laboratory Manual, 1995, Cold Spring Harbor Laboratory Press, Cold Spring Harbor, N.Y.

The first step in the immobilization process is the fabrication of soft metal thin films (about 20 nm) on the substrate of choice (e.g., fused silica, lime glass, quartz, oxidized silicon, etc.). This is done by well known methods such as electron beam evaporation.

After washing and drying, the heterobifunctional spacer arm is absorbed. Various types of heterobifunctional spacers are commercially available or protocols for their synthesis can be found in the literature. Of the different functional groups in the spacer at least one is a soft base to bind the soft metal surface. One other functional group is reactive towards the ligands or biomolecules to be immobilized. All of these chemical groups and reactions are well known to those skilled in the art and some examples are shown in TABLE 2.

TABLE 2

REACTIVE CHEMICAL GROUPS

| Functional Group | Reactive Group |
|---|---|
| Amino | Isothiocyanates |
| | Isocyanates |
| | NHS esters |
| | Carbodiimides |
| Thiol | Haloacetyl derivatives |
| | Maleimides |
| | Disulfide reductants |
| Carboxylate | Carbonyldiimidazole |
| | Carbodiimides |
| Hydroxyl | Epoxides |
| | Carbonyldiimidazole |
| | Isocyanates |

NHS stands for N-hydroxysuccinimide

The functional groups can depend on the type of biomolecule to be immobilized. For example, all proteins contain an amino group on one end and a carboxylate group on the other end, besides all other functional groups provided by the specific amino acids on the sequence. In the case of oligonucleotides these are usually synthesized one nucleotide at a time. Because of this, a single nucleotide label with the desired functional group can be added at some point in the synthesis (usually at the beginning or the end), thus labeling the resulting oligonucleotide. These individual nucleotides can be modified either chemically or enzymatically with any type of functional group in order to provide the desired label. This chemical or enzymatic labeling can be extended to DNA molecules, with the difference that all bases within the molecule targeted by the labeling reaction will be modified. If the desired result is to label the DNA molecule only at one point, the best approach is polymerase chain reaction (PCR) amplification using primers that have been already modified with the desired functional group.

After immobilizing the desired target molecule and performing the desired biochemical application, the molecule can be recovered and the surface regenerated. This can be done by a procedure known as elution. A very common mode of elution of specifically bound molecules is the use of competing molecules, which displace the bound molecule. In order to chose a proper displacer it is important to take into account the nature of the specific interaction. Ligands immobilized through soft metal/soft base interactions on soft metal thin films may be recovered through the use of sulfur-containing competing molecules which displace the heterobifunctional spacers. For example, due to the high aqueous solubility of thiodiglycol and because of its thio-ether functional group, a high elution recovery can be accomplished using a concentrated solution of thiodiglycol. The substrate may then be reused.

The choice of the individual components of the immobilization construct depends upon minimizing nonspecific interactions and steric hindrance, while maximizing binding density. The immobilization construct can either be synthesized on the solid substrate, attached to the PNA, or preformed, in whole or in part, and condensed with the remaining required elements. The most common functional groups are hydroxyl, amino, carboxylate and thiol.

PNA solutions of a specific composition are delivered to specific sites on the solid surface. The functional groups on the solid surface react with the functional groups on the PNA to form a stable bond. This is repeated at different sites on the solid surface using PNA solutions of different compositions, yielding a heterogeneous surface divided into specific reaction sites. Each of these reaction sites contains PNAs, which are complementary to specific sequences of DNA or RNA. This solid surface with the immobilized probe PNA molecules is then contacted with labeled target DNA or RNA solutions. These target molecules are extracted from cells of unknown genetic composition and labeled with molecules (e.g., fluorophores, radioisotopes, etc.) that are easily identified by regular detection methods. The identity of the genetic make-up of these cells is determined by hybridization to their complementary PNA probes of known composition. After the hybridization step, the solid surface is washed to remove any unbound DNA or RNA. The washed surface is then ready for the detection and quantification of the hybridized target by measuring the amount of label on each of the sites.

The following Examples are provided to illustrate specific embodiments of the invention and should not be interpreted so as to limit the scope of the claims.

EXAMPLE 1

Immobilization of Biotinylated Oligonucleotide on a Platinum Surface

Silicon chips with platinum thin films were manufactured by electron beam evaporation. Prior to use, these surfaces are cleansed by using a mixture of 13% RBS 35 solution (Pierce) and 33% ethanol in deionized water. The chips are washed in this solution by immersing in an ultrasonic bath at 50° C. for 20 minutes. This is followed by rinsing three times in deionized water using an ultrasonic bath at 50° C. for 10 minutes. After rinsing the chips are blow-dried under nitrogen or argon.

For this example the heterobifunctional spacer arm was succinimidyl-6-(biotinamido)hexanoate. This molecule is commercially available (Pierce Chemical Co.) or can be synthesized using the information available in the literature (Staros, J. V., *Biochemistry*, 1982, 21(17):3950-3955). This molecule is a derivative of D-Biotin containing an 6-aminocaproic acid spacer arm, about 30.5 Å in length, attached to the valeric acid side chain of biotin and terminating in an NHS ester. This NHS ester reacts with amine groups in proteins and other molecules to form stable amide bond derivatives. Optimal reaction conditions are at pH 7-9. Amine-containing buffers such as Trizma, which may compete in the acylation reaction should be avoided. This spacer arm molecule is insoluble in aqueous reaction conditions and must be dissolved in organic solvents prior to the addition to the aqueous buffered reaction solution. A stock solution may be prepared in either of the organic solvents N,N-dimethylformamide (DMF) or dimethylsulfoxide (DMSO). Addition to the aqueous solution should not exceed 10% organic solvent to avoid precipitation. The molar ratio of the spacer arm molecule to a protein should be 2-50:1 with higher levels resulting in higher incorporation yields.

The chips are then immersed in a 2 mM solution succinimidyl-6-(biotinamido)hexanoate in DMF or ethanol for 12 hours at room temperature. The chips are then washed three times in DMF followed by drying under a stream of nitrogen and immediately used for the immobilization step.

The activated chips are submerged in a 10 mg/ml solution of the amino-labeled oligonucleotide in 0.1 M sodium phosphate, 0.15 M NaCl, at a pH of 7.2 for 30-60 minutes at room temperature, or for several hours at 4° C. The chips are then washed three times in the phosphate buffer followed by drying under a stream of nitrogen.

EXAMPLE 2

Immobilization of a Thiol-Labeled PNA on Gold Surface

Silicon chips with gold thin films were manufactured by electron beam evaporation. Prior to use these surfaces are cleansed by using a mixture of 13% RBS 35 solution (Pierce) and 33% ethanol in deionized water. The chips are washed in this solution by immersing in an ultrasonic bath at 50° C. for 20 minutes. This is followed by rinsing three times in deionized water using an ultrasonic bath at 50° C. for 10 minutes. After rinsing the chips are blow-dried under nitrogen or argon.

For this example the hetrobifunctional spacer arm was dithiobis(succinimidyl-undecanoate). This molecule can be synthesized using the information available in the literature (Wagner, et al., *Biophys. J.*, 1996, 70:2052-2066). The molecule is made up by two molecules each containing a dodecanethiol spacer arm attached to an NHS ester and held together through a disulfide bond. The activation of the soft metal surface has to be done in the presence of a disulfide reductant buffer such as dithiothreitol and dioxane. This breaks the disulfide bond and leads to two heterobifunctional crosslinkers with a NHS ester for binding amino-containing ligands and a thiol group attached to the soft metal surface. The NHS ester reacts with amine groups in proteins and other molecules to form stable amide bond derivatives. Optimal reaction conditions are at pH 7-9. Amine-containing buffers such as Trizma, which may compete in the acylation reaction should be avoided. This spacer arm molecule is insoluble in aqueous reaction conditions and must be dissolved in organic solvents prior to the addition to the aqueous buffered reaction solution.

The activated chips are then immersed in a 1 mM solution of dithio-bis(succinimidylundecanoate) in 1,4-dioxane for 30-60 minutes at room temperature. The chips are then washed three times in 1,4-dioxane followed by drying under a stream of nitrogen and immediately used for the immobilization step.

The activated chips are submerged in a 1 mg/ml solution of the PNA in 0.1 M sodium phosphate, 0.15 M NaCl, at a pH of 7.2 for 30-60 minutes at room temperature, or for several hours at 4° C. The chips are then washed three times in the phosphate buffer followed by drying under a stream of nitrogen.

What is claimed is:

1. A microarray comprising a solid support surface comprising a plurality of reusable ligand-binding specific reaction sites comprising:
   a) a soft metal solid support,
   b) a heterobifunctional spacer comprising a flexible spacer arm and chemi- or physisorbed to said soft metal solid support via soft metal-soft base bonding, wherein said heterobifunctional spacer comprises
      1) an anchor group comprising a soft base selected from the group consisting of succinimidyl-6-(biotinamido)hexanoate and dithiobis(succinimidyl-undecanoate), and
      2) a reactive terminal group selected from the group consisting of an isothiocyanate and an isocyanate, and
   c) a peptide nucleic acid (PNA) linked to said reactive terminal group, wherein said flexible spacer arm allows the PNA to interact with its environment in a way which minimizes any steric hindrance,
   said specific reaction site surfaces comprising PNA solutions of different compositions at different sites on the solid support surface.

2. A microarray comprising a solid support surface of claim 1 in which the soft metal solid support is selected from the group consisting of silver, copper, gold, platinum (II), mercury, mercury (II), thallium, cadmium (II), platinum (IV) and palladium (II) covered surfaces.

3. A microarray comprising a solid support surface of claim 1 in which the heterobifunctional spacer does not contain heteroatoms.

4. A microarray comprising a solid support surface of claim 1 wherein the soft base is selected from the group consisting of an RSH, RS$^-$, R$_2$S, RSSR, CN$^-$, S$_2$O$_3^{2-}$, I$^-$, R$_3$P, (RO)$_3$P, C$_2$H$_4$ and C$_6$H$_6$ group, where R is an organic group.

5. The microarray comprising a solid support surface of claim 1, wherein said specific reaction sites are disposed at a surface density greater than about 100 specific reaction sites per square centimeter and detecting the presence of the biological molecule.

6. A microarray comprising a solid support surface of claim 1, wherein said reactive terminal group is an isocyanate reactive terminal group.

7. A method for preparing a microarray comprising a solid support surface comprising a plurality of reusable ligand-binding specific reaction sites comprising:
   a) selecting a soft metal solid support,
   b) immobilizing at each specific reaction site a heterobifunctional spacer comprising a flexible spacer arm on said solid support via soft metal-soft base bonding, wherein said heterobifunctional spacer comprises
      1) an anchor group comprising a soft base selected from the group consisting of succinimidyl-6-(biotinamido)hexanoate and dithiobis(succinimidyl-undecanoate), and
      2) a reactive terminal group selected from the group consisting of an isothiocyanate, an isocyanate, and an N-hydroxysuccinimide ester, and
   c) attaching at each specific reaction site a PNA to said reactive terminal group of said spacer by addition of PNA in an aqueous solution at a molar ratio of spacer:PNA of between about 2:1 to 50:1, wherein said flexible spacer arm allows the PNA to interact with its environment in a way which minimizes any steric hindrance,
   said specific reaction site surfaces comprising PNA solutions of different compositions at different sites on the solid support surface.

8. A method of claim 7 in which the soft metal solid support is selected from the group consisting of silver, copper, gold, platinum (II), mercury, mercury (II), thallium, cadmium (II), platinum (IV) and palladium (II) covered surfaces.

9. A method of claim 7 in which the heterobifunctional spacer does not contain heteroatoms.

10. A method of claim 7 wherein the soft base is selected from the group consisting of an RSH, RS$^-$, R$_2$S, RSSR, CN$^-$, S$_2$O$_3^{2-}$, I$^-$, R$_3$P, (RO)$_3$P, C$_2$H$_4$ and C$_6$H$_6$ group, where R is an organic group.

11. A method for detecting the presence of a biological molecule comprising exposing a sample containing biological molecules to a solid support surface of claim 1.

12. The method of claim 7 for preparing a microarray comprising a solid support surface, wherein said immobilizing step comprises selecting a reactive terminal group from the group consisting of an isothiocyanate and an isocyanate.

13. The method of claim 7 for preparing a microarray comprising a solid support surface, wherein said immobilizing step comprises selecting an isocyanate for said reactive terminal group.

14. The method of claim 7, wherein said specific reaction sites are disposed at a surface density greater than about 100 specific reaction sites per square centimeter.

* * * * *